United States Patent [19]

Fried et al.

[11] 4,045,485

[45] Aug. 30, 1977

[54] NAPHTHYL ACETALDEHYDE DERIVATIVES; METHODS OF USE THEREOF; AND PROCESSES FOR THE PREPARATION THEREOF

[75] Inventors: John H. Fried; Ian T. Harrison, both of Palo Alto, Calif.

[73] Assignee: Syntex Corporation, Palo Alto, Calif.

[21] Appl. No.: 739,362

[22] Filed: Nov. 5, 1976

Related U.S. Application Data

[60] Division of Ser. No. 566,554, April 9, 1975, abandoned, which is a division of Ser. No. 492,380, July 29, 1974, abandoned, which is a division of Ser. No. 250,733, May 5, 1972, Pat. No. 3,852,363, which is a division of Ser. No. 814,855, April 9, 1969, Pat. No. 3,663,713, which is a continuation-in-part of Ser. No. 741,900, July 2, 1968, Pat. No. 3,626,012.

[51] Int. Cl.² .................... C07C 131/00; C07C 47/56
[52] U.S. Cl. .......................... 260/566 A; 260/600 R
[58] Field of Search ........................... 260/600, 566 A

[56] References Cited

U.S. PATENT DOCUMENTS 2,542,937  2/1951  Miescher et al. .................... 260/599

OTHER PUBLICATIONS

Stork et al., J.A.C.S. 84, 284, 286 (1962).

*Primary Examiner*—Gerald A. Schwartz
*Attorney, Agent, or Firm*—Alan M. Krubiner; William B. Walker

[57] ABSTRACT

2-(2'-Naphthyl) acetaldehyde derivatives optionally substituted at the 2 position and/or positions C-1',4',5',7' or 8'; and/or position C-6' or positions C-5' and 7' exhibit anti-inflammatory, analgesic, antipyretic and antipruritic activity.

3 Claims, No Drawings

NAPHTHYL ACETALDEHYDE DERIVATIVES; METHODS OF USE THEREOF; AND PROCESSES FOR THE PREPARATION THEREOF

This is a division of application Ser. No 566,554, filed Apr. 9, 1975 now abandoned, which in turn is a division of Ser. No 492,380, filed July 29, 1974, abandoned, which in turn is a division of Ser. No. 250,733, filed May 5, 1972, now U.S. Pat. No 3,852,363, which in turn is a division of Ser. No. 814,855, filed Apr. 9, 1969, now U.S. Pat. 3,663,713, which in turn is a continuation in part of Ser. No. 741,900, filed July 2, 1968, now U.S. Pat. No. 3,626,012. This invention pertains to novel naphthyl acetaldehydes and derivatives thereof; to methods of using thereof; and to processes for the preparation thereof.

More particularly, the present novel invention is directed to 2-(2'-naphthyl) acetaldehydes derivatives which exhibit anti-inflammatory, analgesic, antipyretic, and anti-pruritic activity.

The 2-(2'-naphthyl) acetaldehydes derivatives are illustrated by the following formulas (the arabic numbers in formulas I and II designate the position of the 2-(2'-naphthyl) acetaldehyde nomencalture used herein):

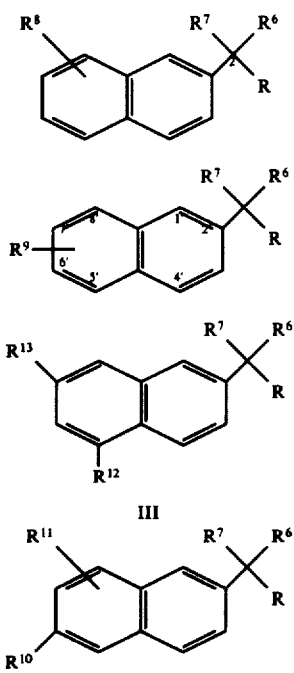

I

II

III

IV wherein, R is —CHR$^1$R$^2$, —CH(OH) (NH$_2$) or —CH(OH) (SO$_3$Y); wherein R$^1$ and R$^2$ are alkoxy, cycloalkoxy, cycloalkylmethoxy, 2-cycloalkylethoxy, 3-cycloalkylpropoxy, monocyclic arylmethoxy, 2-phenylethoxy, 3-phenylpropoxy, alkanoyloxyl, cycloaklaoyloxy, cycloalkyl acetoxy, cycloalkylpropionyloxy, monocyclic arylacetoxy; or R$^1$ and R$^2$ taken together are O, NR$^3$, 3-hydroxyproylene-1,2-dioxy, —OCHR$^4$—CHR$^5$O— or —OCHR$_6$—CR$^4$R$^5$—CHR$_6$O—; wherein R$^3$ is alkyl, cycloalkyl, cycloalkylmethyl, 2-cycloalkyl ethyl, monocyclic arylmethyl, phenethyl, hydroxy, alkoxy, cycloalkoxy, cycloalkyl methoxy, 2-cycloalkylethoxy, benzyloxy, 2-phenylethoxy, amino or carbamoylamino; each of R$^4$ and R$^5$, independently of each other is hydrogen, alkyl, cycloalkyl, cycloalkyl-methyl, 2-cycloalkylethyl, monocyclic arylmethyl, or monocyclic aryl; R$_6$ is hydrogen, methyl; ethyl or propyl; Y is sodium or potassium, one of F$^6$ and R$^7$ is hydrogen, the other is hydrogen, methyl, ethyl or difluoromethyl; or R$^6$ and R$^7$ taken together are methylene, halomethylene or ethylene;

R$^8$ (at position C-1,4 or 8) is hydrogen, alkyl, trifluoromethyl, fluoro, chloro, hydroxy, a conventional hydrolyzable ester, oxyether or thioether;

R$^9$ (at position C-5,6 or 7) is alkyl, cycloalkyl, hydroxymethyl, alkoxymethyl, trifluoromethyl, vinyl, ethynyl, fluoro, chloro, hydroxy, a conventional hydrolyzable ester, oxyether, thioether, formyl, acetyl or monocyclic aryl;

Each of R$^{10}$, R$^{11}$ (at position C-1,4,7 or 8), R$^{12}$ and R$^{13}$ is alkyl, fluoro, chloro, hydroxy, a conventional hydrolyzable ester, oxyether or thioether, provided that when one of R$^{10}$ and R$^{11}$ or one of R$^{12}$ and R$^{13}$ is hydroxy, oxyether or thioether. the other is the identical group or alkyl, fluoro, chloro, or a conventional hydrolyzable ester; and R$^{11}$ (at position C-5) is alkyl, fluoro, chloro, bromo, hydroxy, a conventional hydrolyzable ester, oxyether or thioether; provided when one of R$^{10}$ and R$^{11}$ (at position C-5) is hydroxy, oxyether or thioether, the other in the identical group or alkyl, fluoro, chloro, bromo (R$^{11}$only i.e., only R$^{11}$is bromo, R$^{10}$is not bromo) or a conventional hydrolyzable ester.

In the preferred embodiment of the present invention, R$^1$ and R$^2$ are methoxy, ethoxy, propoxy, cyclopentyloxy, cyclohexyloxy, benzyloxy, phenethyloxy, tolyloxy, acetoxy, propionlyloxy, valeryloxy, caproyloxy, cyclopentylcarbonyloxy, cyclohexylcarbonyloxy, phenylacetoxy or tolylacetoxy; or R$^1$ and R$^2$ taken together are O, methylimino, ethylimino, isopropylimino, cyclopentylimino, cyclohexylimino, benzylimino, p-methylbenzylimino, phenethylimino, phenylimino, tolylimino, hydroxylimino, methoxyminio, ethoxyimino, i-propoxyimino, cyclophentyloxyimino, cyclohexyloxyimino, benzyloxyimino, p-methylbenzyloxyimino, phenethyloxyimino, aminoimino, carbamoylamino, ethylenedioxy, 1, 2-propylenedioxy, 1,3-propanedioxy, 3-hydroxypropylene-1,2-dioxy, 2,3-butanedioxy, 1,2-diphenylethylenedioxy, 1,2-dicyclopentylethylenedioxy, 1,2-dibenzylethylenedioxy, 2,2-dimethyl-1,3-propanedioxy or 2-phenyl-1,3-propanedioxy; Y is sodium; one of R$^6$ and R$^7$ is hydrogen, the other is hydrogen, methyl or difluoromethyl; or R$^6$ and R$^7$ taken together are methylene or difluoromethylene; R$^8$ (at position C-1,4 or 8) is hydrogen, methyl, ethyl, isoproyl, trifluoromethyl, fluoro, chloro, methoxy, methoxymethyloxy, difluoromethoxy, methylthio, methoxymethylthio or difluoromethylthio R$^9$ (at position C-5,6 or 7) is methyl, ethyl, isopropyl, cyclopropyl, trifluoromethyl, vinyl, ethynyl, fluoro, chloro, methoxy, methoxymethyloxy, difluoromethoxy, methylthio, methoxymethylthio or difluoromethylthio; each of R$^{10}$, R$^{11}$ (at position C-1,4,7 or 8), R$^{12}$ and R$^{13}$ is methyl, ethyl, isopropyl, fluoro, chloro, methoxy, methoxymethoxy, difluoromethoxy, methylthio, methoxymethylthio, or difluoromethylthio, provided that when one of R$^{10}$or R$^{11}$, or one of R$^{12}$and R$^{13}$is methoxy, methoxymethyloxy, difluoromethoxy, methylthio, methoxymethylthio or difluoromethylthio, the other is the identical group or methyl, ethyl, isopropyl, fluoro or chloro; and R$^{11}$ (at position C-5) is methyl, ethyl, isopropyl, fluoro, chloro, methoxy, methoxymethyloxy, difluoromethoxy, methylthio, methoxymethylthio or difluoromethylthio; provided when one of $R^{10}$ and $R^{11}$ (at position C-5) is methoxy, methoxymethyloxy, difluoromethoxy, methylthio, methoxymethylthio, or difluoromethylthio, the other is the identical group or methyl, ethyl, isopropyl, fluoro, chloro or bromo ($R^{11}$ only). $R^{11}$ (at position C-5) is methyl, ethyl, isopropyl, fluoro, chloro, bromo, trifluoromethyl, methoxy, methoxymethyloxy, difluoromethoxy, methylthio, methoxymethylthio or difluoromethylthio, the other is the identical group or methyl, ethyl, isopropyl, fluoro, chloro or chloro ($R^{11}$ only).

By the term "alkyl" is meant branched or straight chain hydrocarbon atoms, such as methyl, ethyl, propyl, isopropyl, butyl, tertiarybutyl, pentyl, hexyl, and the like. By the term "cycloalkyl" is meant cyclic hydrocarbon groups of three to seven carbon atoms, such as cyclopropyl, cyclopentyl, cyclohexyl, and the like.

The term "monocyclic aryl" defines a phenyl group optionally substituted with one to two methyl, ethyl, isopropyl, methoxy, hydroxy, fluoro, or chloro groups. Typical monocyclic aryls include phenyl, 2-tolyl, 3-tolyl, 4-tolyl, 2,4-dimethylphenyl, 2,6-dimethylphenyl, 3-ethylphenyl, 4-ethylphenyl, 4-isopropylphenyl, 2-methoxy, 4-methoxyphenyl, 2,4-dimethoxyphenyl, 3-hydroxyphenyl, 2,6-dihydroxyphenyl, 2-chlorophenyl, 2,6-dichlorophenyl, 3-fluorophenyl, 4-fluorophenyl, 2,4-difluorophenyl; 2,3-difluorophenyl, 2,3,4-trifluorophenyl, parachlorophenyl, 2,4-dihydroxyphenyl, 2,4-dimethoxyphenyl and the like.

The term "alkanoyloxy" defines a straight or branched saturated hydrocarbon carbonyloxy group of from 1 to 12 carbon atoms. Typical alkanoyloxy groups include acetoxy, propionuyloxy, butyryloxy, 4-methylvalryloxy, capropyloxy, 2-methylbutylryloxy, capryloxyloxy, pelargyloxy, capryloxy, 9-methylcapryloxy, lauroyloxy, and the like.

The term "alkoxy" defined a straight or branched chain hydrocarbon ether group of six or less carbon atoms, including methoxy, ethoxy, 2-propoxy, propoxy, butoxy, 3-pentoxy, and the like. By the term "alkoxymethyloxy" is meant methylether groups substituted with one alkoxy group; typical alkoxymethyloxy groups include methoxymethyloxy, ethoxymethyloxy, isopropoxymethyloxy, and the like.

By the term "alkylthio" jis meant straight or branched chain hydrocarbon thioether groups of six or less carbon atoms, including methylthio, ethylthio, propylthio, 2-propylthio, 2-butylthio, pentylthio, 3-hexylthio, and the like. By the term "alkoxymethylthio" is meant methylthio ether groups substituted with one alkoxy group, such as methoxymethylthio, ethoxymethylthio, 2-propoxymethylthio, and the like.

The term "cycloalkyloxy" defines a cyclic hydrocarbon ether group of from three to sever carbon atoms. Typical cycloalkyloxy include cyclopentyloxy and cyclohexyloxy.

By the term "monocylic aralkyloxy" is meant an alkoxy substituent substituted with one monocyclic aryl group. Typical monocyclic aralkyloxy include: 2,6-dimethylbenzyloxy and p-chlorophenylthyloxy.

The term "alkanoyloxy" defines an alkylcarbonyloxy group. Typical alkanoyloxy groups include acetoxy, butyryloxy, and capryloxy. The term "cycloalkanoyloxy" defines a monocyclic cycloalkylcarbonyloxy group. The term "monocyclic aralkanoyloxy" defines an aralkyl carbonyloxy group such as phenylacetyloxy.

By the term "halomethylene" is meant non- or dihalomethylene groups wherein halo is fluoro or chloro. The preferred halomethylenes include fluoromethylene, difluoromethylene, fluorochlormethylene and chloromethylene.

The term "conventional hydrolyzable ester", as used herein, denotes those hydrolyzable ester groups conventionally employed in the art, preferably those derived from hydrocarbon carboxylic acids or their salts. The term "hydrocarbon carboxylic acid" defines both substituted and unsubstituted hydrocarbon carboxylic acids. These acids can be completely saturated or possess varying degrees of unsaturation (including aromatic), can be of straight chain, branched chain, or cyclic structure and preferably contain from one to twelve carbon atoms. Typical conventional hydrolyzable esters thus included within the scope of the term and the instant invention are acetate, propionate, 2-methyl propionate, butyrate, valerate, caproate, enanthate, caprylate, benzoate, phenylacetate, diethylacetate, trimethylacetate, t-butylacetate, cyclohexylacetate, cyclopentylpropionate, adamantoate, bicyclo-[2.2.2]octyl carboxylate, hemisuccinate, hemiadipate, hemi-$\beta$, $\beta$-dimethylflutarate, and the like.

The term "oxyether", as used herein, denotes those ether groups conventionally employed in the art, preferably those derived from straight chain, branched chain, aromatic hydrocarbons and oxo heterocylic hydrocarbons. The term "hydrocarbon" defines both saturated and unsaturated hydrocarbons. These designated hydrocarbons are optionally substituted with groups such as hydroxy, alkoxy, halo, alkylthio, and the like. Preferably the hydrocarbons contain from one to twelve carbon atoms. Typical oxyethers thus include alkoxy, difluoromethoxy, alkoxymethyloxy, tetrahydrofuran-2'-yloxy, tetrahydropyran-2'-yloxy and 4'-alkoxytetrahydropyran-4'-yloxy.

The term "thioether", as used herein, denotes those thio ether groups conventionally employed in the art, preferably those derived from straight chain, branched chain, cyclic and aromatic hydrocarbons. The term "hydrocarbon" defines both saturated and unsaturated hydrocarbons. These hydrocarbons are optionally substituted with groups such as hydroxy, alkoxy, alkylthio, halo and the like. Preferably the hydrocarbons contain from one to twelve carbon atoms. Typical thioethers thus include alkylthio, difluoromethylthio, alkoxymethylthio, and the like.

When one of $R^6$ and $R^7$ is hydrogen and the other is methyl, ethyl or difluoromethyl, the compounds of formulas I, II, III and IV exist as pairs of enantiomorphs. Each enantiomorph or optical isomer of the compounds of formulas I, II, III and IV is included within the present invention. In some instances, one enantiomorph exhibits greater anti-inflammatory, analgesic, anti-pyretic and/or anti-pruritic activity than the corresponding other enantiomorph. Nevertheless, the present compounds of formulas I, II, III and IV tht exist as pair of enantiomorphs can be administered as mixtures of enantiomorphs or as individual resolved enantiomorphs.

Preferably the individual resolved enantiomorphs or optical isomers of the compounds of formulas I, II, III and IV are prepared from the corresponding individual resolved enantiomorphs or optical isomers of the starting material. Alternatively, the optical isomers can be resolved by conventional means, such as selective biological degradation. The resolved enantiomorph of formulas I, II, III and IV and the corresponding resolved starting material will not necessarily have the same optical rotation although they will have the same absolute configuration.

The 2-(2'-naphthyl) acetldehydes and derivatives thereof of formulas I, II, III and IV exhibit anti-inflammatory, analgesic, anti-pyretic and anti-pruritic activity. Accordingly, these compounds are employed in the present method of effecting treatment of inflammation, pain, pyrexia and pruritus in mammals, such as mice, rats, dogs, monkeys or humans.

These compounds are useful in the treatment of inflammation of the skin, respiratory tract, muscular-skeletal system, joints, internal organs, and tissues. Accordingly, these compounds are useful in the treatment of conditions characterized by inflammation, such as contact dermatitis, allergic conditions, burns, rheumatism, contusion, arthritus, bone fracture, post-traumatic conditions and gout. In those cases in which the above conditions include pain, pyrexia and pruritus, coupled with the inflammation, the instant compounds are useful for relief of these conditions as well as the inflammation. The instant compounds are useful in the treatment of pain associated with post-operative conditions, post-traumatic conditions, post-partum conditions, dysmenorrhea, burns, gout, contusions, neuralgia, neuritis, headache and rheumatic fever. As stated above, these compounds also exhibit anti-pyretic activity; accordingly, these compounds are useful in the treatment of pyrexia where reduction of a fever is indicated, for example, in the treatment of high fevers associated with diseases such as rheumatic fever, bronchitis, pneumonia, typhoid fever, and Hodgkin's disease. The present compounds are also useful in the treatment of pruritus where the condition exists contemporaneously with inflammation, pain and/or fever. Moreover, the compounds are useful for treating pruritus per se.

Although the above compounds of formulas I-IV exhibit anti-inflammatory, analgesic, anti-pyretic and anti-pruritic activity, certain groups of the above compounds exhibit remarkably enhanced specific activity while retaining the other types of activity. For example, the compounds of formula II where $R^9$ is at position C-6 exhibit enhanced anti-inflammatory activity together with analgesic, anti-pyretic and anti-pruritic activity. Accordingly, the compounds of formula II would be very useful in treating a condition characterized by a high degree of inflammation together with moderate degree of pain. The 5 and 7 substituted compounds of formula II and the compounds of formula IV exhibit superior analgesic activity together with anti-inflammatory, anti-pyretic and anti-pruritic activity. Accordingly, the 5 and 7 substituted compounds of formula I and the compounds of formula IV are very useful to treat conditions characterized by a high degree of pain together with a moderate degree of inflammation, fever and pruritus.

The preferred manner of oral administration provides the use of a convenient daily dosage regimen which can be adjusted according to the degree of affliction. Generaly, a daily dose of from 0.01 mg. to 100 mg. of the active compound per kilogram of body weight of the mammal is employed. Most conditions respond to treatment comprising a dosage level in the order of 1 mg. to 5 mg. per kilogram of body weight per day. For such oral administration, a pharmaceutically acceptable non-toxic composition formed by the incorporation of any of the normally employed excipients. Suitable pharmaceutical excipients include starch, glucose, lactose, sucrose, gelatin, malt, rice, flour, chalk, silica gel, magnesium carbonate, magnesium stearate, sodium stearate, glyceryl monostereate, talc, sodium chloride, dried skim milk, glycerol, propylene glycol, water, ethanol, and the like. These compositions take the form of solutions, suspensions, tablets, pills, capsules, powders, sustained release formulations, and the like. In addition, these compounds can be administered in conjunction with other medicinal agents depending upon the specific condition being treated.

A measure of anti-inflammatory activity according to the carrageenin induced edema assay of Winter et al., *Proceedings of the Society for Experimental Biology and Medicine III*, 544 (1962) shows the following: that 2-(6'-methoxy-2'-naphthyl) propionaldehyde to have over three times the activity of phenylbutazone; that the semicarbazone of 2-(6'-methoxy-2'-naphthyl) propionaldehyde has over three times the activity of phenyl butazoned; that 1-hydroxyimino-2-(6'-methoxy-2'-naphthyl) propane has over two times the activity of phenylbutazone; that 1,1-dimethyl-2-(6'-methoxy-2'-naphthyl) propane is as active as phenylbutazone; and that the sodium bisulfite addition product of 2-(6'-methoxy-2'-naphthyl) propionaldehyde has about three times the activity of henylbutazone.

Similar standard assays to measure anti-pyretic activities show 2-(6'-methoxy-2'-naphthyl) propionaldehyde and the sodium bisulfite addition product thereof to have over fourteen and seventeen times, respectively, the anti-pyretic activity of aspirin.

Included within the compounds of formulas I, II, III and IV are the novel 2-(2'-naphthyl) acetaldehyde derivatives of the following formulas:

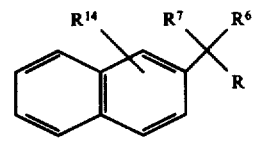

V

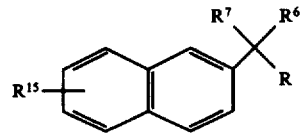

VI

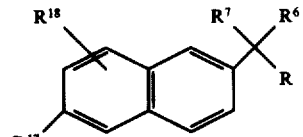

VIII

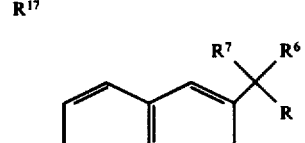

VII

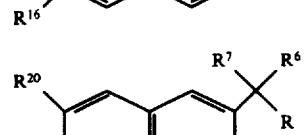

IX wherein,
R, $R^6$ and $R^7$ are as defined above.

$R^{14}$ (at position C-1, 4 or 8) is trifluoromethyl, fluoro, chloro, hydroxy, a conventional hydrolyzable ester or thioether;

$R^{15}$ (at position C-5 or 7) is alkyl, cycloalkyl, hydroxymethyl, alkoxymethyl, trifluoromethyl, vinyl, ethynyl, fluoro, chloro, hydroxy, a conventional hydrolyzable ester, oxyether, thioether, formyl, acetyl or aryl;

$R^{16}$ is alkyl, cycloaklyl, hydroxymethyl, alkoxymethyl, trifluoromethyl, vinyl, ethynyl, fluoro, chloro, hydroxy, a conventional hydrolyzable ester, alkoxymethyloxy, difluoromethoxy, tetrahydropyran-2'-yloxy, tetrahydrofuran-2'-yloxy, 4'-alkoxy-tetrahydropyran-4'-yloxy; thioether, formyl, acetyl or aryl; and each of $R^{17}$ and $R^{18}$ (at positions C-1,4,7 or 8), $R^{19}$ and $R^{20}$ is alkyl, fluoro, chloro, hydroxy, a conventional hydrolyzable ester, oxyether or thioether; provided that when one of $R^{17}$ or $R^{18}$, or one of $R^{19}$ or $R^{20}$ is hydroxy, oxyether or thioether the other is the identical group or alkyl, fluoro, or chloro or a conventional hydrolyzable ester; and $R^{18}$ (at position C-5) is alkyl, fluoro, chloro, bromo, hydroxy, a conventional hydrolyzable ester, oxyether or thioether; provided when one of $R^{17}$ and $R^{18}$ (at position C-5) is hydroxy, oxyether or thioether the other is the identical group or alkyl, fluoro, chloro, bromo ($R^{18}$ only), or a conventional hydrolyzable ester.

In the preferred embodiment of the novel compounds of formulas V, VI, VII, VIII and IX, $R^1$ and $R^2$ are methoxy, ethoxy, cyclopentyloxy, cyclohexyloxy, benzyloxy, phenethyloxy, tolyloxy, acetoxy, propionyloxy, valeryloxy, caproloxy, cyclopentylcarbonyloxy, cyclohexylcarbonyloxy, phenylacetyloxy or tolylacetoyloxy; or $R^1$ and $R^2$ taken together are =O, methylimino, ethylimino, isopropylimino, cyclopentylimino, cyclohexylimino, benzylimino, p-methylbenzylimino, phenethylimino, phenylimino, tolylimino, hydroxyimino, methoxyimino, ethoxyimino, isopropoxyimino, cyclopentyloxyimino, cyclohexyloxyimino, benzyloxyimino, p-methylbenzyloxyimino, phenethyloxyimino, aminoimino, carbamoylamino, ethylenedioxy, 1,2-propylenedioxy, 1,3-propanedioxy, 3-hydroxypropylene-1,2-dioxy, 2,3-butanedioxy, 1,2-diphenylethylenedioxy, 1,2-dicyclopentylethylenedioxy, 1,2-dibenzylethylenedioxy, 2,2-dimethyl-1,3-propanedioxy or 2-phenyl-1,3-propanedioxy; Y is sodium; one of $R^6$ and $R^7$ is hydrogen, the other is hydrogen, methyl or difluoromethyl; or $R^6$ and $R^7$ taken together are methylene or difluoromethylene; $R^{14}$ (at position C-1,4 or 8) is trifluoromethyl, fluoro, chloro, methylthio, methoxymethylthio or difluoromethylthio; $R^{15}$ (at position C-5 or 7) is methyl, ethyl, isopropyl, cyclopropyl, trifluoromethyl, vinyl, ethynyl, fluoro, chloro, methoxy, methoxymethyloxy, difluoromethoxy, methylthio, methoxymethylthio or difluoromethylthio; $R^{16}$ is methyl, ethyl, isopropyl, cyclopropyl, trifluoromethyl, vinyl, ethynyl, fluoro, chloro, methoxymethyloxy, difluoromethoxy, methylthio, methoxymethylthio or difluoromethylthio; each of $R^{17}$, $R^{18}$ (at position C-1,4,7 or 8), $R^{19}$ and $R^{20}$ is methyl, ethyl, isopropyl, fluoro, chloro, methoxy, methoxymethyloxy, difluoromethoxy, methylthio, methoxymethylthio or difluoromethylthio; provided that when one of $R^{17}$ or $R^{18}$, or one of $R^{19}$ or $R^{20}$ is methoxy, methoxymethyloxy, difluoromethoxy, mthylthio, methoxymethylthio, or difluoromethylthio, the other is the identical group of methyl, ethyl, isopropyl, fluoro or chloro; and $R^{18}$ (at position C-5) is methyl, ethyl, isopropyl, fluoro, chloro, bromo, methoxy, methoxymethyloxy, difluoromethoxy, methylthio, methoxymethylthio or difluoromethylthio; provided when one of $R^{17}$ and $R^{18}$ (at position C-5) is methoxy, methoxymethyloxy, difluoromethoxy, methylthio, methoxymethylthio or difluoromethylthio, the other is the identical group of methyl, ethyl, isopropyl, fluoro, chloro or bromo ($R^{18}$ only i.e., only $R^{18}$ is bromo, $R^{17}$ is not bromo).

An especially preferred group of novel 2-(2'-naphthyl) acetaldehyde derivatives are those of formulas VI, VII, VIII and IX wherein R, $R^1$, $R^2$, $R^6$, $R^7$, $R^{15}$, $R^{16}$, $R^{17}$, $R^{18}$, $R^{19}$ and $R^{20}$ are defined in the above immediate paragraph.

The present compounds of formulas I, II, III and IV (wherein R is CHO) are prepared from the corresponding 2-naphthyl acetic acid derivatives or esters thereof via a novel process which can be illustrated by the following reaction scheme A:

SCHEME A

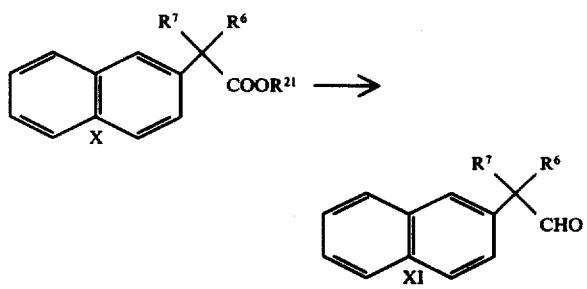

wherein, $R^6$ and $R^7$ are as defined above and $R^{21}$ is hydrogen or alkyl. In the above scheme, the naphthyl moiety of the 2-(2'-npahthyl) acetic acid derivatives of formula X and of the 2-(2'-naphthyl) acetaldehyde derivatives of formula XI are substituted with 1) a $R^8$ group at position C-1,4 or 8; 2) a $R^9$ group at position C-5,6 or 7; 3) a $R^{10}$ at position C-6 and a $R^{11}$ t position C-1,4,5,7 or 8; or 4) a $R^{12}$ and $R^{13}$ group at positions C-5 and C-7 respectively.

The novel process of Scheme A is conducted by treating the starting compound of formula X, a 2-(2'-naphthyl) acet.c acid derivative or ester thereof, with lithium aluminum hydride in an inert organic ether solvent, such as diethyl ether, tetrahydrofuran, and the like. If a free 2-(2'-naphthyl) acetic acid derivative is used as a starting material, at least 0.75 molar equivalents of lithium aluminum hydride are used, nd preferably about 1.0 to 2.5 molar equivalents are used. If an ester of a 2-(2'-naphthyl) acetic acid derivative is used as a starting material, at least 0.5 molar equivalents of lithium aluminum hydride are used, and preferably about 0.6 to 2.0 molar equivalents are used. The reduction is carried out at a temperature between 0° C and the boiling point of the solvent employed, preferably between 15° C to 35° C. The second step of the above process consists of adding ethyl acetate to the reaction mixture diluting the resulting mixture with water (at least 8 ml of water per gram of alkali metal hydride), filtering and evaporating it. The resulting residue is treated with chromium trioxide in acetic acid or pyridine or acetone containing 8N sulfuric acid. The process is carried out at a temperature between 0° C and 50° C, preferably the reaction temperature is between 5° C and 30° C. At least 1 molar equivalents of chromium trioxide are used per molar equivalent of the acid starting material and preferably about 1.5 to about 2.5 molar equivalents of chromium trioxide are used.

Alternatively, the first step can be carried out by treating the compound of formula X with diborane in tetrahydrofuran at about room temperature. One to two molar equivalents of diborane per molar equivalent of the starting compound are usually sufficient.

Alternatively, the second step can be carried out by treating the residue obtained from the first step of the reaction with dicyclohexylcarbodiimide (DCC) and anhydrous phosphoric acid in dimethyl sulfoxide at about room temperature. Generally, three molar equivalents of DCC and ½ molar equivalents of anhydrous phosphoric acid are used per molar equivalent of the starting compound of formula X used in the first step.

At the completion of the above process, the compound of formula XI, the product, is isolated by conventional means. For example, the reaction mixture is extracted with ethyl acetate; the extract is filtered, washed to neturality, dried and evaporated. The product can be further purified by conventional techniques such as crystallization or chromatography.

Certain groups present in the starting compound of formula X are reduced by lithium aluminum hydride or diborane. For example, an acetyl group is reduced to α-hydroxy ethyl group and a formyl group is reduced to a hydroxy methyl group. These reduced groups are regenerated after the completion of the first step of the above process via an oxidation process using manganese dioxide (active) in an inert solvent, such as acetone, petroleum ether, and the like, at about room temperature.

In the second step of the above process, certain groups will be oxidized. For example, hydroxymethyl and hydroxy groups will be oxidized. These groups can be advantageously protected by esterifying these groups prior to the oxidation step of Scheme A. The groups can be regenerated after the above process by hydrolysis of the esterified groups such as with an aqueous base, such as aqueous sodium carbonate.

The acetals of the compounds of formula XI are prepared by treating the aldehyde products with alcohols, such as methanol, propanol, butanol, isopentanol, neopentanol, hexanol, isohexanol, cyclopropanol, cyclobutanol, cyclopentanol, cyclobutylmethanol, cyclohexylmethanol, 2-cyclopropylethanol, 2-cyclohexylethanol, 3-cyclopropylpropanol, 3-cyclopentylpropanol, phenylmethanol, p-tolylmethanol, 3-chlorophenylmethanol, 3,5-dihydroxyphenylmethanol, 2,4-diethylphenylmethanol, 4-methoxyphenylmethanol, 2-phenylethanol, 3-phenylpropanol, 1,2-butandiol, 1,3-butandiol, 1,4-butandiol, 2,3-butandiol, 1,2,4-butantriol, 2-n-butyl-2-ethyl-1,3-propanediol, 2,2-diethyl-1,3-propanediol, 2,2-dimethyl-1,3-propanediol, 2,2-diphenyl-1,3-propanediol, 2-ethyl-1,3-hexanediol, 2-ethyl-2-methyl-1,3- propanediol, 2-methyl-2-propyl-1,3-propanediol, 1,2-pentanediol, 2,3-pentanediol, 2,2-dimethyl-1,3-pentanediol, 3-methyl-2,4-pentanediol, 2,3-hexanediol, 3,4-hexanediol, 2-ethyl-1,3-hexanediol, 3-methyl-2,4-heptanediol,2,3-octanediol, 4,5-octanediol, ethyleneglycol, 1,2-propanediol, 1,2-octanediol, 2,3-nonanediol, 4,5-nonanediol, 1,2-dodecanediol, 2,3-dodecanediol, 6,7-dodecanediol, 1,2-decanediol, cyclopentylethyleneglycol, 1,2-dicyclohexylethyleneglycol, 3-cyclopropyl-1,2-propanediol, 1-cyclobutyl-2,3-hexanediol, 4-cyclopentyl-1,2-butanediol, 1,6-dicyclopentyl-4,5-hexanediol, 1,3-dicyclopropyl-1,2-propanediol, 1-cyclopentyl-5-cyclohexyl-2,3-pentanediol, 3-phenyl-1,2-propanediol, 1-(4'-tolyl)-2,3-tridecanediol, 1-cyclohexyl-3-(2'-methoxy -henyl)-1,2-propanediol, 1-cyclopentyl-4-(3'-chlorophenyl)-2,3-butanediol, 1-cyclopropyl-5-(4'-hydroxyphenyl)-2,3-pentanediol, 1,4-di(2',6'-dimethylphenyl)-2,3-butanediol, phenylethyleneglycol, 1-(4'-ethylphenyl)-2,3-heptanediol, 1-cyclohexyl-2-phenylethyleneglycol, 1-cyclopentyl-3-phenyl-2,3-propanediol, 1-cyclobutyl-4-(4'-isopropylphenyl)-3,4-butanediol, 1,3-diphenyl-1,2-propanediol, 1,2-diphenylethyleneglycol, 1,3-propanediol, 2-methyl-1,3-propanediol, 2-cyclohexyl-1,3-propanediol, 2-cyclopentylmethyl-1,3-propanediol, 2-(2'-cyclopropylethyl)-1,3-propanediol, 2-benzyl-1,3-propanediol 2-phenyl-1,3-propanediol, 2,2-dimethyl-1,3-propanediol, 2,2-diethyl-1,3-propanediol, 2,2-dipropyl-1,3-propanediol, 2,2-dipentyl-1,3-propanediol, 2-methyl-2-ethyl-1,3-propanediol, 2-methyl-2-propyl-1,3-propanediol, 2-ethyl-2-propyl-1,3propanediol, 2-ethyl-2-butyl-1,3-propanediol, 2,2-dicyclopentyl-1,3-propanediol, 2,2-di(-cyclohexylmethyl)-1,3-propanediol, 2-cyclohexylethyl-2-hexyl-1,3-propanediol, 2,2-dibenzyl-1,3-propanediol, 2,2-diphenyl-1,3-propanediol, 2-ethyl-2-(3'-tolyl)-1,3-propanediol, 2-(4'-methylbenzyl)-2-(4'-tolyl)-1,3-propanediol, 2,4-pentanediol, 3,5-heptanediol, 4,6-nonanediol, 2-ethyl-2-butyl-1,3-propanediol, 2,2-diethyl-1,3-butanediol, 2-hexyl-2-cyclohexyl-1,3-butanediol, 3-methyl-2-cyclohexyl-2,4-pentanediol, 2,2-di(cyclopropylmethyl)-1,3-pentanediol, 3,3-dimethyl-2,4-pentanediol, 3,3-diphenyl-2,4-pentanediol, 3,3-dihexyl-2,4-pentanediol, 3-methyl-3-phenyl-2,4-pentanediol, 3-cyclopropyl-2,4-hexanediol, 2-(3'-ethylphenyl)-1,3-hexanediol, 3,3-dibenzyl-2,4-hexanediol, 3-(4'-methoxyphenyl)-2,4-heptanediol, 4,4-diethyl-3,5-heptanediol, 4,4-dicyclohexyl-3,5-heptanediol, 3,3-di(cyclohexylethyl)-2,4-heptanediol, 4-benzyl-4-phenyl-3,5-heptanediol, 4-cyclobutylethyl-3,5-octanediol, 4,4-dimethyl-3,5-octanediol, 4-cyclohexylmethyl-4-benzyl-3,5-octanediol, 5-cyclopentylmethyl-4,6-nonanediol, 5,5-dipropyl-4,6-nonanediol, 5,5-dipentyl-4,6-nonanediol, ethanol, 2-propanol, propanol, 2-pentanol, ethylene glycol, 1,2-propylene glycol, propane-1,3-diol, glycerine and the like, in the presence of an acid catalyst, such as p-toluenesulfonic acid, perchloric acid and the like.

The oxime derivatives of the compounds of formula XI are prepared by refluxing the aldehyde product with hydroxylamine hydrochloride or monosubstituted hydroxylamine hydrochloride in the presence of pyridine in absolute ethanol to yield the corresponding oxime or 1-monosubstituted oxyimino derivatives. The product is isolated by evaporating the reaction mixture. The product is further purified by crystallization or chromatography. Typical monosubstituted hydroxylamine hydrochlorides used in the process include the hydrochloride salts of methoxyamine, butoxyamine, 2-butoxyamine, pentoxyamine, 3-pentoxyamine, hexoxyamine, cyclopropoxyamine, cyclobutoxyamine, cyclohexoxy, cyclopentylmethoxyamine, cyclohexylmethoxyamine, 2-cyclopentylethoxyamine, 2-cyclohexylethoxyethoxyamine, cyclopropylethoxyamine, cyclobutylmethoxyamine, benzyloxyamine, 2-phenylethoxyamine, and the like. The hydrazone derivatives of the compounds of formula XI are prepared by treating the aldehyde product with hydrazine in the presence of sulfuric acid or hydrochloric acid in methanol or ethanol. The semicarbazone derivatives of the compounds of formula XI are prepared by heating the aldehyde products with an unsubstituted or substituted semicarbazide hydrochloride salt and sodium acetate in ethanol and water. The semicarbazone, hydrazone and oxime derivatives of the compounds of formula XI can be further purified by recrystallization from ethanol-water. When the 2-(2'-naphthyl) acetaldehyde derivative is substituted with an acetyl group, only 1.1 molar equivalents of semicarbazine hydrochloride, hydrazone or hydroxylamine hydrochloride is employed and the product is purified by chromatographing on alumina or silica.

The hydroxy amino derivatives of the compounds of formula XI are prepared by treating the aldehyde products with anhydrous ammonia gas in an anhydrous solvent such as diethylether. The resulting hydroxy amino derivatives are isolated by filtration.

The bisulfite addition derivatives of the compounds of formula XI are prepared by treating the aldehyde products with a saturated aqueous solution of sodium bisulfite. The bisulfite addition derivatives can be purified by crystallization.

The unsubstituted and substituted imino derivatives of the compounds of formula XI are prepared by treating the aldehyde product with anhydrous ammonia or a monosubstitute amine in a halogenated hydrocarbon solvent at a temperature of from about −70° C to about 50° C, preferably at 0° C to give the corresponding 1-(unsubstituted or substituted) amino-2-(2'-naphthyl) ethanol derivative. The latter is heated between about 30° C and 150° C, preferably about 50° C, under reduced pressure to yield the corresponding 1-(unsubstituted or substituted)-imino derivatives. Typical monosubstituted amines that are used include: methylamine, propylamine, hexylamine, isopentylamine, cyclopropylamine, cyclobutylmethylamine, cyclopentylmethylamine, 2-cyclopropylethylamine, 2-cyclohexylethylamine, benzylamine, 4'-methylbenzylamine, 2', 6'-difluorobenzylamine, phenethylamino and the like.

When a resolved optical isomer of a 2-(2'-naphthyl) acetic acid starting compound of formula IX is employed in the above process, the corresponding resolved optical isomer of the compound of formula X is obtained.

The 2-(2'-naphthyl) acetic acid starting materials of formula X are known and can be prepared by any one of several methods fully described in our co-pending U.S. application Ser. Nos. 608,997, filed Jan. 13, 1967; 694,771, filed Dec. 7, 1967 and 741,858, filed July 2, 1968.

One method is to treat a 1-tetralone, optionally substituted at position C-5,6,7 or 8, or disubstituted at position C-6 and C-5,7 or 8, sequentially with (1) an alkyl carbonate and an alkali metal hydride, (2) an alkali metal hydride and an α-haloacetic acid and (3) an aqueous mineral acid to obtain the corresponding 2-(carboxymethyl)-1-tetralone. The latter is reduced with sodium borohydride to form the corresponding 1,2,3,4-tetrahydro-1-hydroxy-2-naphthyl acetic acid; this resulting product is hydrogenolyzed wih hydrogen in the presence of a hydrogenation catalyst, such as a palladium catalyst; the resulting product is esterified and then dehydrogenated with palladium on charcoal catalyst at about 180° C to furnish the corresponding 2-naphthyl acetic acid ester derivative.

The starting compounds of formula X that are substituted at position C-1 are prepared from the corresponding 2-(carbomethoxymethyl)-1-tetralones by treating the latter (1) with a phosphorous pentahalide to introduce a halo group at the C-1 position or (2) with alkyl magnesium bromide and then with aqueous mineral acid to alkylate at the C-1 position or (3) with trialkyl orthoformate in the presence of an acid catalyst to add an alkoxy group at position C-1; and then dehydrogenating the resulting halogenated or alkylated or alkoxylated product by refluxing with 2,3-dichloro-5,6-dicyano-1,4-benzoquinone. By employing 6-substituted-2-(carbomethoxymethyl)-1-tetralones in the above processes, the corresponding 1-substituted-6-substituted compounds of formula IX are prepared.

The starting compounds of formula IX substituted at position C-4 or disubstituted at positions C-4 and 6 are prepared from unsubstituted and 6-substituted 3-(carbomethoxymethyl) tetralones, respectively, via the process used to prepare 1-substituted-2-naphthyl acetic acids from 2-(carboxymethyl) tetralones. 2-(Carboxymethyl) tetralones are prepared via the process described in J. Chem. Soc. (London) 1922, 1717.

The 2-naphthyl acetic acid starting materials that are substituted at C-5 or C-7 with cycloalkyl, hydroxymethyl, alkoxymethyl, vinyl, ethynyl, formyl, acetal, or monocyclicalkyl group are prepared from the corresponding C-5 or C-6 substituted 1-tetralones, which are prepared, by conventional methods or the methods described in our copending U.S. application Ser. No. 694,771, filed on Dec. 7, 1967, employed in the preparation of 1-tetralones, similarly substituted at C-6. For example, a 5-methyl-1-tetralone is ketalized with ethylene glycol and p-toluenesulfonic acid and then treated with N-bromo succinimide to yield the corresponding 5-bromomethyl derivative which is deketalized by acid hydrolysis. The 5-bromomethyl compounds are treated with potassium acetate in dimethylformamide, and then hydrolyzed with aqueous base to yield the corresponding 5-hydroxymethyl-1-tetralones. The 5-hydroxymethyl group is etherified by conventional means; such as treating the 5-hydroxymethyl-1-tetralone with sodium hydride and methyl iodide to obtain the corresponding 5-methoxymethyl-1tetralone. The 5-hydroxymethyl-1-tetralone is ketalized and oxidized with manganese dioxide to yield the corresponding 5-formyl-1-tetralone ketal compound. When the latter is treated with methylmagnesium bromide the corresponding 5-(1'-methyl-1'-hydroxymethyl)-1-tetralone ketal is obtained, which when dehydrated with heat in the presence of acid yields the corresponding 5-vinyl-1 -tetralone. The 5-ethynyl-1-tetralone is prepared by treating the corresponding 5-vinyl compound with a molar equivalent of bromine and then debrominating the resulting dibromo product with potassium hydroxide. The 5-acetal-1-tetralone is prepared by oxidizing the 5-(1'-methyl-1'-hydroxymethyl)-1-tetralone with chromium trioxide in 8N sulfuric acid. The 5-cycloalkyl-1-tetralone is prepared by treating the corresponding 5-chloro-1-tetralone with ethylene glycol and p-toluenesulfonic acid and then with magnesium in tetrahydrofuran to yield the corresponding Grignard reagent; this in turn is treated with the corresonding oxoalkyl, such as cyclohexanone, to obtain the corresponding 5-(1'-hydroxycycloalkyl)-1-tetralone ketal. The latter is acid hydrolyzed and then hydrogenolyzed with a molar equivalent of hydrogen in the presence of Raney Nickel to yield the corresponding 5-cycloalkyl compound. The 5-aryl-1-tetralones can be prepared by treating 1-tetralòn-5-yl magnesium chloride ketal, prepared as described above, with an unsubstituted or substituted cyclohexenone in tetrahydrofuran to yield the corresponding 5-(unsubstituted or substituted)cyclohexadienyl-1tetralone ketal, which upon a mild dehydrogenation in the presence of 5% palladium on charcoal at about 175° C and acid hydrolysis yields the corresponding 5-(unsubstituted or substituted)-phenyl-1-tetralone. Similarly, the 7-substituted-1-tetralones can be prepared from 7-methyl-1-tetralone and 7-chloro- or 7-bromo-1-tetralone by means of the above described processes.

The disubstituted 2-(2'-naphthyl) acetic acid derivatives of formula X are prepared by the methods disclosed in our copending U.S. Application Ser. Nos. 608,997 filed Jan. 13, 1967, 694,771 filed Dec. 7, 1967 and 741,858 filed July 2, 1968. For example, 2-(5',6'-disubstituted-2'-naphthyl) acetic acid derivatives are prepared by treating methyl phenylacetate with at least 2 molar equivalents of a 2-substituted succinic anhydride, such as 2-methoxy succinic anhydride, and at least 2 molar equivalents of aluminum chloride in nitrobenzene or carbon disulfide to yield the corresponding methyl p-(3'-carboxy-3'-substituted-1'-oxopropyl) phenyl acetate and methyl p-(3'-carboxy-2'-substituted-1'-oxopropyl) phenyl acetate derivatives. The derivatives are separated by conventional means, such as by chromatography or distillation. The 1 oxo group of the 2'-substituted derivative is selectively reduced with sodium borohydride to a 1'-hydroxy group. The 1'-hydroxy derivatives is esterified by treatment with acetic anhydride in pyridine. The resulting 1'-acetoxy derivative is treated with thionyl chloride, phosphorus trichloride or phosphorus pentachloride to yield the corresponding methyl p-(3'-chlorocarbonyl-2'-substituted-1'-acetoxypropyl) phenyl acetate derivative, which when treated with at least 3 -molar equivalents of aluminum chloride in benzene yields the corresponding 7-carbomethoxymethyl-4-acetoxy-3-substituted-1-tetralone, which is selectively reduced with sodium borohydride to give the corresponding methyl 2-(5'-acetoxy-6'-substituted-8'-hydroxy-5',6',7',8'-tetrahydro-2'-naphthyl) acetate. The latter is esterified with acetic anhydride and pyridine and selectively hydrogenolyzed with a molar equivalent of hydrogen in the presence of a palladium catalyst to yield methyl 2-(5'-acetoxy-6'-substituted-5',6',7',8'-tetrahydro-2'-naphthyl) acetate derivative, which is hydrolyzed with aqueous base, such as with 5% aqueous sodium bicarbonate solution, and esterification with diazomethane to yield the corresponding methyl 2-(5'-hydroxy-6'-substituted-5',6',7',8'-tetrahydro-2'-naphthyl) acetate derivative. The latter is treated with at least 2 molar equivalents of N,N-diethyl-N-(1,1,2-trifluoro-2-chloroethyl) amine in methylene chloride and then it is refluxed with 2,3-dichloro-5,6-dicyano-1,4-benzoquinone in xylene to yield the corresponding methyl 2-(5'-fluoro-6'-substituted-2'-naphthyl) acetate. The 5'-hydroxy derivatives is heated with a thioalkane in the presence of acid at about 180° C in a sealed container to yield the corresponding methyl 2-(5'-alkylthio-6'-substituted-2'-naphthyl) acetate. The 5'-hydroxyl derivative is oxidized with chromium trioxide in acetic acid to yield the corresponding methyl 2-(5'-oxo-6'-substituted-2'-naphthyl) acetate derivative. The 5'-oxo derivative is treated with phosphorus pentachloride and then refluxed in 2,3-dichloro-5,6-dicyano-1,4-benzoquinone in xylene to yield the corresponding 2-(5'-chloro-6'-substituted-2'-naphthyl) acetic acid. The 5'-chloro derivative is refluxed with cuprous bromide in dimethyl sulfoxide to yield the corresponding methyl 2-(5'-bromo-6'-substituted-2'-naphthyl) acetate derivative; by employing cuprous iodide in place of cuprous bromide, the corresponding 5'-iodo derivative is obtained. The 5'-oxo derivative is treated with at least a molar equivalent of an alkyl magnesium bromide, then acid hydrolyzed and finally heated with 5% palladium on charcoal to about 180° C to yield the corresponding 2-(5'-alkyl-6'-substituted-2'-naphthyl) acetic acid. The 5'-oxo derivative is treated with trialkyl orthoformate in the presence of an acid catalyst, such as p-toluenesulfonic acid in an aryl hydrocarbon solvent, and then it is refluxed with DDQ in xylene to yield the corresponding methyl 2-(5'-alkoxy-6'-substituted-2'-naphthyl) acetate derivative. The 3'-substituted-1'-oxo derivative, prepared as described above, is selectively reduced with sodium borohydride, treated with thionyl chloride or the like, treated with aluminum chloride in benzene, esterified with acetyl chloride, selectively reduced with sodium borohydride, dehydrogenolyzed, and hydrolyzed with aqueous base, as described above, to yield the corresponding methyl 2-(5'-hydroxy-7'-substituted-5',6',7', 8'-tetrahyro-2'-naphthyl) acetic derivative. The latter is treated as described above to dehydrogenate and introduce the C-5' fluoro, chloro, bromo, alkyl, alkoxy and alkylthio groups.

The compounds of formula X substituted at the 2-position are prepared from the corresponding 2-unsubstituted compounds of formula X by esterifying the latter, and treating it with ethyl formate and sodium metal to obtain the corresponding 2,2-hydroxy-methylene derivative. The latter is treated with sodium hydride, then with chlorine gas, then with chromium trioxide in acetic acid and then heated to yield the corresponding 2-chloro derivative. The 2-(2-chloro-2-naphthyl) acetic acid derivative is refluxed in sodium hydroxide, esterified with diazomethane, oxidized with chromium trioxide in acetic acid and coupled by refluxing with difluoromethylene triphenyl phosphorane in benzene to obtain the corresponding 2,2-difluoromethylene derivatives of formula IX.

The 2-methyl substituents are added to the 2-unsubstituted compounds of formula X by esterifying the latter and treating it with sodium hydride and alkyl halide, such as methyl iodide. The 2-difluoromethyl substituent is added by treating the 2-unsubstituted compounds of formula X successively with sodium hydride and diethyl carbonate, then with chlorodifluoromethane, then with aqueous 5% sodium hydroxide at 75° C followed by acidification with aqueous mineral acid and then finally heating the resulting product to about 150° C to yield the corresponding 2-difluoromethyl derivatives of formula X.

The 2,2-methylene substituents are introduced by treating the 2-unsubstituted compounds of formula X with formaldehyde and an alkali metal hydroxide. The 2,2-ethylene substituents are introduced by refluxing the corresponding 2,2-methylene derivatives of formula X with diiodomethane in the presence of zinc-copper couple.

The various substituted tetralones are known can be prepared by conventional methods. For example, the 5,7-distributed tetralones are prepared by treating a 1,3-disubstituted benzene derivatives with 2 or more molar equivalents of succinic anhydride and two or more molar equivalents of aluminum chloride in nitro benzene or carbon disulfide to obtain the corresponding 4-oxo-4-(2',4'-disubstituted phenyl) butyric acids. The latter are reduced with a reading agent such as sodium borohydride or one molar equivalent of hydrogen in the presence of platinum to reduce the 4-oxo group to a 4-hydroxy group. The resulting hydroxy compounds are further hydrogenalized with a molar equivalent of hydrogen in the presence of platinum catalyst to yield the corresponding 4-(2',4'-disubstituted phenyl) butyric acids. These compounds are cyclized by refluxing with thionyl chloride and then treated with three or more equivalents of aluminum chloride to yield the corresponding 5,7-disubstituted 1'-tetralones. When the benzene starting material is substituted with two different groups, two tetralones are obtained. For example, if the starting material is 1-chloro-3-methyl benzene, 5-chloro-7-methyl-1-tetralone and 5-methyl-7-chloro-1-tetralone are obtained. The compounds are separated by conventional techniques, such as distillation or chromatogrophy, including gas-liquid chromatography.

The 2-naphthyl acetic acids of formula X that exist as enantiomorphs can be resolved by preparing the alkaloid base salts of the latter, resolving the resulting diastero-isomer salts by fractional crystallization and cleaving the resolved salts. The optical rotation of a particular 2-naphthyl acetic acid is determined by polarimetry.

The following examples are included to further illustrate the present invention and are not intended as limitations of the present invention.

PREPARATION 1

A mixture of 1925 g. of 1-chloro-2-methoxynaphthalene, 80 g. of acetyl chloride, 400 g. of aluminum chloride and 2.5 liters of nitrobenzene are stirred for 60 hours at room temperature. The temperature mixture is then washed with dilute hydrochloric acid, dried over sodium sulfate and evaporated to yield 2-acetyl-5-chloro-6-methoxynaphthalene. The resulting acetyl product is added to a mixture of 39 g. of sulfur and 105 g. of morpholine and heated to about 150° C for 3 hours. The mixture is then added to 1 liter of concentrated hydrochloric acid and refluxed for 3 hours. The mixture is then cooled, diluted with 6 liters of ice-water and extracted with methylene chloride. The extracts are combined, washed with water to neutrality, dried over sodium sulfate and evaporated to yield 2-(5'-chloro-6'-methoxy-2'-naphthyl) acetic acid.

In a similar manner,
2-(5',6'-dimethyl-2'-naphthyl) acetic acid,
2-(5'-bromo-6'-methoxy-2'-naphthyl) acetic acid,
2-(5'-iodo-6'-methoxy-2'-naphthyl) acetic acid,
2-(5',6'-dimethoxy-2'-naphthyl) acetic acid,
2-(5'-methylthio-6'-chloro-2'-naphthyl) acetic acid, and
2-(5'-fluoro-6'-methoxy-2'-naphthyl) acetic acid, are prepared from the corresponding 1,2-disubstituted naphthalene by means of the above described process.

To a mixture of 50 g. of 2-(5'-chloro-6'-methoxy-2'-naphthyl) acetic acid and 250 ml. of diethyl ether, there are added 9 g. of diazomethane in 250 ml. of diethyl ether. The mixture is stirred for 1 hour and then flushed with nitrogen gas until colorless. The mixture is then evaporated to yield methyl 2-(5'-chloro-6'-methoxy-2'-naphthyl) acetate.

To a mixture of 4.8 g. of sodium hydride in 100 ml. of 1,2-dimethoxyethane, there are added 53 g. of the above methyl ester product. The mixture is stirred for 2 hours; then 19 g. of methylbromide in 200 ml. of 1,2-dimethoxyethane are slowly added. The resulting mixture is stirred for 3 hours at 25° C; it is then diluted with 1 l. of ice-water and extracted with diethyl ether. The extracts are combined, washed with water dried over sodium sulfate and evaporated to yield methyl 2-(5'-chloro-6'-methoxy-2'-naphthyl) propionate.

EXAMPLE 1

To a mixture of 0.4 g. of lithium aluminum hydride and 100 ml. of ethyl ether, a mixture of 2.3 g. of d and l 2-(6'-methoxy-2'-naphthyl) propionic acid and 100 ml. of ethyl ether. The mixture is stirred at 0° C for 30 minutes, then 10 ml. of ethyl acetate are added; one hour later 18.5 ml. of water are added. The resulting mixture is filtered and evaporated under reduced pressure. The resulting residue is added to a mixture of 10 g. of chromium trioxide and 1 liter of pyridine. The resulting reaction mixture is stirred under anhydrous conditions for 24 hours at 25° C, then 1 liter of ethyl acetate is added. The resulting ethyl acetate mixture is filtered, washed with an aqueous saturated solution of sodium bisulfite and water to neutrality, dried over sodium sulfate and evaporated under reduced pressure to yield a racemic mixture of 2-(6'-methoxy-2'-naphthyl)propionaldehyde.

By employing a resolved 2-(2'-naphthyl) acetic acid derivative in the above process, the corresponding 2-(2'-naphthyl) acid aldehyde derivatives will be obtained. For example, if R 2-(6'-methoxy-2'-naphthyl)-propionaldehyde is prepared from R 2-(6'-methoxy-2'-naphthyl)propionic acid and S 2-(6'-methoxy-2'-naphthyl)propionaldehyde is prepared from S 2-(6'-methoxy-2'-naphthyl)propionic acid [these compounds have been named in accordance with the Cahn-Ingold-Prelog system of naming optical isomers; see R. S. Cahn, C. K. Ingold and V. Prelog, "Experientia", Vol. 12, 81–95 (1956) and Carl R. Noller, "Chemistry of Organic Compound", pp. 368–370, W. B. Saunders Co., Philadephia (196)].

Similary, 2-(1'-trifluoromethyl-2'-naphthyl)-propionaldehyde, 2-(4'-fluoro-2'-naphthyl)-butanal, 2-(5'-methoxy-2'-naphthyl)-propionaldehyde, 2-(5'-methyl-2'-naphthyl)-acetaldehyde. 2-(5'-chloro-2'-naphthyl)-propionaldehyde, 2-(5'-methylthio-2'-naphthyl)-2,2-methylacetaldehyde, 2-(6'-methylthio-2'-naphthyl)2-difluoromethyl acetaldehyde, 2-(6'-methoxy-2'-naphthyl)-2-difluoromethyl acetaldehyde, 2-(6'-methyl-2'-naphthyl)-propionaldehyde, 2-(6-ethynyl-2'-naphthyl)-propionaldehyde, 2-(6'-acetyl-2'-naphthyl)-2,2-methylene acetaldehyde, 2-(6'-chloro-2'-naphthyl)-propionaldehyde 2-(7'-methyl-2'-naphthyl)-propionaldehyde, 2-(7'-methoxy-2'-naphthyl)-acetaldehyde, 2-(7'-chloro2'-naphthyl)-propionaldehyde, 2(7'-methylthio-2'-naphthyl)-2,2-methylene acetaldehyde, 2-(8'-ethylthio-2'-naphthyl)-butanal, 2-(5'-chloro-6'-methoxy-2'-naphthyl)acetaldehyde, 2-(5'-chloro-6'-methoxy-2'-naphthyl) propionaldehyde, 2-(5'-bromo-6'-methoxy-2'-naphthyl) propionaldehyde, 2-(5',7'-dichloro-2'-naphthyl)acetaldehyde, 2-(1'-fluoror-6'-methoxy-2'-naphthyl)-propionaldehyde and 2'-(5',7'-dimethyl-2'-naphthyl) propionaldehyde are prepared from the corresponding substituted 2-naphthyl acetic acids.

EXAMPLE 2

A mixture of 230 g. of 2-(5'-methoxy-2'-naphthyl) acetic acid, 57 g. of lithium aluminum hydride and 10 liters of tetrahydrofuran is stirred for two hours at 10° C, then 1 liter of ethyl acetate is added. After one hour, 500 ml. of water is added to the resulting mixture, the mixture is stirred, filtered, dried over sodium sulfate and evaporated under vacuum. The residue is added to a mixture of 620 g. of dicyclohexyl carbodiimide, 50 g. of anhydrous phosphoric acid and 2 liters of dimethylsulfoxide. The resulting mixture is stirred for eight hours, then added to water, filtered to remove dicyclohexyl urea and extracted with ether. The combined ether extracts are filtered, washed with water to neutrality, dried over sodium sulfate and evaporated to yield 2-(5'-methoxy-2'-naphthyl) acetaldehyde.

Similarly,
2-(1'-methoxy-2'-naphthyl) acetaldehyde,
2-(4'-difluoromethylthio-2'-naphthyl) propionaldehyde,
2-(5'-fluoro-2'-naphthyl) acetaldehyde,
2-(5'-methylthio-2'-naphthyl) propionaldehyde,
2-(5'-chloro-2'-naphthyl) acetaldehyde,
2-(5'-trifluoromethyl-2'-naphthyl)-2,2-difluoromethylene acetaldehyde,
2-(6'-fluoro-2'-naphthyl) propionaldehyde,
2-(6'-methyl-2'-naphthyl) acetaldehyde,
2-(6'-methoxy-2'-naphthyl) acetaldehyde,
2-(6'-difluoromethoxy-2'-naphthyl)-2-difluoromethyl acetaldehyde,
2-(6'-difluoromethoxy-2'-naphthyl) acetaldehyde,
2-(6'-methoxy-2'-naphthyl) butanal,
2-(7'-fluoro-2'-naphthyl)-2-propionaldehyde,
2-(7'-vinyl-2'-naphthyl)-2-propionaldehyde,
2-(7'-methylthio-2'-naphthyl)-2-butanal,
2-(7'-methylthio-2'-naphthyl) acetaldehyde
2-(7'-chloro-2'-naphthyl)-2,2-methylene acetaldehyde,
2-(8'-trifluoromethyl-2'-naphthyl)-2,2-methylene acetaldehyde,
2-(5',7'-dimethoxy-2'-naphthyl) propionaldehyde,
2-(5',6'-dimethyl-2'-naphthyl) propionaldehyde, and
2-(5'-bromo-6'-methoxy-2'-naphthyl) propionaldehyde are prepared, respectively, from the corresponding compounds by means of the above process:
2-(1'-methoxy-2'-naphthyl) acetic acid,
2-(4'-difluoromethylthio-2'-naphthyl) propionic acid,
2-(5'-fluoro-2'-naphthyl) acetic acid,
2-(5'-methylthio-2'-naphthyl) propionic acid,
2-(5'-chloro-2'-naphthyl) acetic acid,
2-(5'-trifluoromethyl-2'-naphthyl)-2,2-difluoromethylene acetic acid,
2-(6'-fluoro-2'-naphthyl) propionic acid,
2-(6'-methyl-2'-naphthyl) acetic acid,
2-(6'-methoxy-2'naphthyl) acetic acid,
2-(6'-difluoromethoxy-2'-naphthyl)-2-difluoromethyl acetic acid,
2-(6'-difluoromethoxy-2'-naphthyl) acetic acid,
2-(6'-methoxy-2'-naphthyl) butyeric acid,
2-(7'-fluoro-2'-naphthyl) propionic acid,
2-(7'-vinyl-2'-naphthyl) propionic acid,
2-(7'-methylthio-2'-naphthyl) butyeric acid,
2-(7'-methylthio-2'-naphthyl) acetic acid,
2-(7'-chloro-2'-naphthyl)-2,2-methylene acetic acid,
2-(8'-trifluoromethyl-2'-naphthyl)-2,2-methylene acetic acid,
2-(5',7'-dimethoxy-2'-naphthyl) propionic acid,
2-(5',6'-dimethyl-2'-naphthyl) propionic acid, and
2-(5'-bromo-6'-methoxy-2'-naphthyl) propionic acid, respectively, by means of the above process.

EXAMPLE 3

A mixture of 46 g of 2-(7'-methoxy-2'-naphthyl) propionic acid, in 200 ml. of tetrahydrofuran is treated with 6 g of diborane in 500 ml of tetrahydrofuran and stirred for one hour at room temperature (about 23° C). The mixture is allowed to stand for one hour after being diluted with 50 ml. of aqueous acetone, the1 1 liter of diethyl ether are added. The resulting mixture is washed with water, dried over sodium sulfate and evaporated. The resulting residue is added to a mixture is stirred under anhydrous conditions for 24 hours at 25° C; then 1 liter of ethyl acetate is added. The mixture is then filtered, washed with an aqueous acidified solution of sodium bisulfite and water to neutrality, dried over sodium sulfate and evaporated under reduced pressure to yield 2-(7'-methoxy-2'-naphthyl) propionaldehyde.

Similarly,
2-(5'-methyl-2'-naphthyl) propionaldehyde,
2-(5'-difluoromethoxy-2'-naphthyl) propionaldehyde,
2-(5'-difluoromethoxy-2'-naphthyl) acetaldehyde,
2-(5'-methylthio-2'-naphthyl) acetaldehyde,
2-(6'-ethyl-2'-naphthyl) propionaldehyde,
2-(6'-chloro-2'-naphthyl)-2-difluoromethyl acetaldehyde,
2-(6'-vinyl-2'-naphthyl)-2,2-methylene acetaldehyde,
2-(6'-methylthio-2'-naphthyl) acetaldehyde,
2-(6'-trifluoromethyl-2'-naphthyl) acetaldehyde,
2-(7'-cyclopropyl-2'-naphthyl) propionaldehyde,
2-(7'-acetyl-2'-naphthyl) propionaldehyde,
2-(7'-fluoro-2'-naphthyl) acetaldehyde,
2-(7'-trifluoromethyl-2'-naphthyl) propionaldehyde,
2-(1'-chloro-2'-naphthyl) butyrylaldehyde,
2-(4'-ethoxy-2'-naphthyl)-2,2-ethylene acetaldehyde,
2-(6',7-dimethoxy-2'-naphthyl) propionaldehyde,
2-(5',7'-dimethyl-2'-naphthyl) acetaldehyde, and
2-(8'-methoxy-2'-naphthyl) propionaldehyde, are prpared from
2-(5'-methyl-2'-naphthyl) propionic acid,
2-(5'-difluoromethoxy-2'-naphthyl) propionic acid,
2-(5'-difluoromethoxy-2'-naphthyl) acetic acid,
2-(5'-methylthio-2'-naphthyl) acetic acid,
2-(6'-ethyl-2'-naphthyl) propionic acid,
2-(6'-chloro-2'-naphthyl)-2-difluoromethyl acetic acid,
2-(6'-vinyl-2'-naphthyl)-2,2-methylene acetic acid,
2-(6'-methylthio-2'-naphthyl) acetic acid,
2-(6'-trifluoromethyl-2'-naphthyl) acetic acid,
2-(7'-cyclopropyl-2'-naphthyl) propionic acid,
2-(7'-acetyl-2'-naphthyl) propionic acid,
2-(7'-fluoro-2'-naphthyl) acetic acid,
2-(7'-trifluoromethyl-2'-naphthyl) propionic acid,
2-(1'-chloro-2'-naphthyl) butyric acid,
2-(4'-ethoxy-2'-naphthyl)-2,2-ethylene acetic acid,
2-(6',7'-dimethoxy-2'-naphthyl) propionic acid,
2-(5',7'-dimethyl-2'-naphthyl) acetic acid, and
2-(8'-methoxy-2'-naphthyl) propionic acid, respectively, by means of the above process.

EXAMPLE 4

By means of the process of Examples 1, 2 or 3, the following 2-(2'-naphthyl) acetaldehyde derivatives are prepared from the corresponding 2-(2'-naphthyl) acetic acid derivatives or the esters thereof:
2-(1'-ethoxy-2'-naphthyl)-2,2-difluoromethylene acetaldehyde,
2-(1'-propyl-2'-naphthyl)-2-chloromethyl acetaldehyde,
2-(1'-hexylthio-2'-naphthyl)-2-chloromethyl acetaldehyde,
2-(1'-methoxymethylthio-2'-naphthyl) acetaldehyde,
2-(1'-i-propyl-2'-naphthyl) butanal,
2-(1'-pentoxymethyloxy-2'-naphthyl)-2,2-ethylene acetaldehyde,
2-(1'-fluoro-2'-naphthyl) propionaldehyde, 2-(4'-hexyl-2'-naphthyl)-2-fluoromethyl acetaldehyde,
2-(4'-i-propyl-2'-naphthyl)-2,2-ethylene acetaldehyde,
2-(4'-tetrahydropyran-2''-yloxy-2'-naphthyl)-2-chloromethyl,
2-(4'-methoxy-2'-naphthyl) acetaldehyde,
2-(4'-isopropoxymethylthio-2'-naphthyl)-2-chloromethyl acetaldehyde,
2-(4'-chloro-2'-naphthyl)-2,2-methylene acetaldehyde,
2-(4'-propylthio-2'-naphthyl) propionaldehyde,
2-(4'-acetoxy-2'-naphthyl)-2,2-difluoromethylene acetaldehyde,
2-(5'-pentyl-2'-naphthyl) acetaldehyde,
2-(5'-cyclopropyl-2'-naphthyl)-2,2-difluoromethylene acetaldehyde,
2-[5'-(4''-methoxytetrahydropyran-4''-yloxy)-2'-naphthyl] butanal,
2-(5'-acetyl-2'-naphthyl)-2,2-methyleneacetaldehyde,
2-(5'-p-tolyl-2'-naphthyl) acetaldehyde,
2-(6'-trifluoromethyl-2'-naphthyl) propionaldehyde,
2-(6'-ethyl-2'-naphthyl) propionaldehyde,
2-(6'-methoxymethyloxy-2'-naphthyl)-2,2-difluoromethylene acetaldehyde,
2-(6'-cyclohexyl-2'-naphthyl) propionaldehyde,
2-(6'-p-tolyl-2'-naphthyl)-2,2-ethylene acetaldehyde,
2-(7'-i-propoxy-2'-naphthyl)-2-fluoromethyl acetaldehyde,
2-(7'-formyl-2'-naphthyl) propionaldehyde,
2-(7'-acetyl-2'-naphthyl) acetaldehyde,
2-(7'-propionyloxy-2'-naphthyl)-2-difluoromethyl acetaldehyde,
2-(7'-phenyl-2'-naphthyl) propionaldehyde,
2-(7'-cyclopentyl-2'-naphthyl) butanal,
2-(8'-tetrahydrofuran-2''-yloxy-2'-naphthyl)-2-fluoromethyl acetaldehyde,
2-(8'-butyl-2'-naphthyl)-2,2-methylene acetaldehyde,
2-(8'-pentoxymethylthio-2'-naphthyl) butanal,
2-(8'-ethoxymethylthio-2'-naphthyl)-2,2-methylene acetaldehyde,
2-(8'-trifluoromethyl-2'-naphthyl) acetaldehyde,
2-(8'-ethoxymethoxy-2'-naphthyl)-2,2-difluoromethylene acetaldehyde,
2-(8'-caproxy-2'-naphthyl)-2'-difluoromethyl acetaldehyde,
2-(1',6'-diethoxy-2'-naphthyl)-2,2-difluoromethylene acetaldehyde,
2-(4'-butyl-6'-methoxymethylthio-2'-naphthyl) acetaldehyde,
2-(5'-chloro-6'-methoxy-2'-naphthyl) acetaldehyde,
2-(6'-chloro-8'-propylthio-2'-naphthyl) propionaldehyde,
2-(5'-fluoro-6'-methoxy-2'-naphthyl) propionaldehyde,
2-(5'-iodo-6'-methoxy-2'-naphthyl) propionaldehyde,
2-(1'-methyl-2'-naphthyl) propionaldehyde,
2-(1'-chloro-2'-naphthyl) acetaldehyde,
2-(4'-methylthio-2'-naphthyl) propionaldehyde,
2-(4'-methyl-2 -naphthyl) propionaldehyde,
2-(5'-ethyl-2'-naphthyl) propionaldehyde,
2-(5'-trifluoromethyl-2'-naphthyl) acetaldehyde,
2-(5'-trifluoromethyl-2'-naphthyl) propionaldehyde,
2-(5'-i-propyl-2'-naphthyl) acetaldehyde,
2-(5'-cyclobutyl-2'-naphthyl) acetaldehyde,
2-(5'-vinyl-2'-naphthyl) acetaldehyde,
2-(5'-fluoro-2'-naphthyl) propionaldehyde,
2-(5'-methylthio-2'-naphthyl) acetaldehyde,
2-(6'-ethyl-2'-naphthyl) acetaldehyde,
2-(6'-isopropyl-2'-naphthyl) acetaldehyde,
2-(6'-cyclopropyl-2'-naphthyl) acetaldehyde,
2-(6'-fluoro-2'-naphthyl) acetaldehyde,
2-(6'-chloro-2'-naphthyl) acetaldehyde,
2-(6'-isopropoxymethyloxy-2'-naphthyl)-2-fluorochloromethyl acetaldehyde,
2-(6'-formyl-2'-naphthyl)-2,2-difluoromethylene acetaldehyde,
2-(5'-pentoxymethylthio-2'-naphthyl)-2-fluorochloromethyl acetaldehyde,
2-(6'-vinyl-2'-naphthyl) acetaldehyde,
2-(6'-ethylthio-2'-naphthyl) acetaldehyde,
2-(6'-methylthio-2'-naphthyl) propionaldehyde,
2-(6'-tetrahydrofuran-2''-yloxy-2'-naphthyl) propionaldehyde,
2-(7'-i-propyl-2'-naphthyl) propionaldehyde,
2-(7'-methyl-2'-naphthyl) acetaldehyde,
2-(7'-ethyl-2'-naphthyl) acetaldehyde,
2-(7'-cyclopropyl-2'-naphthyl) acetaldehyde,
2-(7'-trifluoromethyl-2'-naphthyl) acetaldehyde,
2-(7'-chloro-2'-naphthyl) acetaldehyde,
2-(7'-vinyl-2'-naphthyl) propionaldehyde,
2-(7'-ethylthio-2'-naphthyl) acetaldehyde,
2-(7'-methylthio-2'-naphthyl) propionaldehyde,
2-(7'-butylthio-2'-naphthyl)-2-difluoromethyl acetaldehyde,
2-(7'-ethynyl-2'-naphthyl)-2,2-methylene acetaldehyde,
2-(8'-methoxymethyloxy-2'-naphthyl)-2,2-difluoromethylene acetaldehyde,
2-(5',7'-dimethoxy-2'-naphthyl) acetaldehyde,
2-(5',6'-dichloro-2'-naphthyl) propionaldehyde, and
2-(6',7'-dimethylthio-2'-naphthyl) acetaldehyde.

EXAMPLE 5

A mixture of 5 g. of 2-(5'-methoxy-2'-naphthyl) acetaldehyde, 150 ml. of anhydrous benzene, 60 ml. of ethylene glycol (distilled over sodium hydroxide) and 0.8 g. of p-toluenesulfonic acid monohydrate is refluxed for 12 hours with a water trap. Aqueous sodium bicarbonate solution is then added to the cooled mixture and the organic phase is separated, washed with water, dried over anhydrous sodium sulfate and evaporated to dryness to yield ethylenedioxy 2-(5'-methoxy-2'-naphthyl) ethane which is recrystallized from acetone:hexane.

Similarly, by employing glycerine, 2,3-dihydroxybutane, 2,2-dimethyl-1,3-dihydroxypropane, 2,2-diethyl-1,3-dihydroxypropane, 2,2-diphenyl-1,3-dihydroxypropane, 2,2-dicyclopentyl 1,3-dihydroxypropane, 2-cyclohexylmethyl-1,3-dihydroxypropane, 2-ethyl-2-(2'-cyclopropylethyl)-1,3-dihydroxypropane, 1,3-dihydroxypropane, 3,4-dihydroxyhexane, 2,3-dihydroxynonane and 2,4-dihydroxypentane in place of ethylene glycol in the above process, the corresponding glycerol, butane-2,3-dioxy, 2,2-dimethylpropane-1,3-dioxy, 2,2-diethylpropane-1,3-dioxy, 2,2-diphenylpropane-1,3-dioxy, 2,2-dicyclopentylpropane-1,3-dioxy, 2-cyclohexylmethylpropane-1,3-dioxy, 2-ethyl-2-(2'-cyclopropylethyl)propane-1,3-dioxy, propane-1,3-dioxy, hexane-3,4-dioxy, nonane-2,3-dioxy, and pentane-2,4-dioxy cyclic acetals of 2-(5'-methoxy-2'-naphthyl) acetaldehyde, respectively, are obtained.

By employing the 2-(2'-naphthyl) acetaldehyde derivatives prepared in Examples 1, 2, 3 and 4 in the above process, the corresponding ethylenedioxy cyclic acetals thereof are obtained.

EXAMPLE 6

A mixture of 21 g. of 2-(6'-methoxy-2'-naphthyl) propionaldehyde, 500 ml. of ethanol and 20 drops of perchloric acid are allowed to stand for eight hours at room temperature under anhydrous conditions. The mixture is then diluted with 500 ml. of aqueous 1% sodium bicarbonate; and extracted with methylene chloride. The combined extracts are washed with water to neutrality, dried over magnesium sulfate and evaporated to yield 1,1-diethoxy-2-(6'-methoxy-2'-naphthyl) propane.

1,1-Dimethoxy-2-(6'-methoxy-2'-naphthyl) propane, 1,1-dipropoxy-2-(6'-methoxy-2'-naphthyl) propane, 1,1-diisopropoxy-2-(6'-methoxy-2'-naphthyl) propane, 1,1-dipentoxy-2-(6'-methoxy-2'-naphthyl) propane, 1,1-dicyclopropoxy-2-(6'-methoxy-2'-naphthyl) propane, 1,1-dicyclopentoxy-2-(6'-methoxy-2'-naphthyl) propane, 1,1-dicyclohexoxy-2-(6'-methoxy-2'-naphthyl) propane,1,1-dibenzyloxy-2-(6'-methoxy-2'-naphthyl) propane, and 1,1-diphenethoxy-2 -(6'-methoxy-2'-naphthyl) propane are similarly prepared by employing methanol, propanol, isopropanol, pentanol, cyclopropanol, cyclopentanol, cyclohexanol, benzyl alcohol and pheneethanol respectively, in place of ethanol in the above process.

By using the 2-(2'-naphthyl) acetaldehyde derivatives prepared in Examples 1, 2, 3 and 4 in the above process, the corresponding diethoxy acetals thereof are obtained.

EXAMPLE 7

Water is added to a solution of 20.1 g. of 2-(6'-methoxy-2'-naphthyl) acetaldehyde and 500 ml. of ethanol until the solution is faintly turbid; the turbidity is removed by the addition of several drops of ethanol. To this resulting solution then is added 25 g. of semicarbazide hydrogenchloride and 50 g. of sodium acetate. The resulting mixture is refluxed for 10 minutes and then is allowed to cool at 0° C for 24 hours. The cooled mixture is then filtered and the resulting crystals are washed with several protions of ice cold ethanol to yield the semicarbazone of 2-(6'-methoxy-2'-naphthyl) acetaldehyde. The semicarbazone is recrystallized from water:ethanol (3:1).

In a similar manner, the semicarbazones of the 2-(2'-naphthyl) acetaldehyde derivatives of Examples 1, 2, 3 and 4 are prepared by means of the above process. For example, the semicarbazone of 2-(5'-methoxy-2'-naphthyl) acetaldehyde is prepared by employing 2-(5'-naphthyl) acetaldehyde in the above process.

EXAMPLE 8

A mixture of 50 g. of 2-(5'-methoxy-2'-naphthyl) acetaldehyde, 50 g. of hydroxylamine hydrogenchloride, 500 ml. of pyridine and 500 ml. of absolute ethanol are refluxed for 8 hours. The resulting mixture is cooled and evaporated under reduced pressure. The resulting residue is triturated with 250 ml. of cool water; the resulting aqueous mixture is then filtered. The resulting crystals are washed thoroughly with several portions of water to yield 2-(5'-methoxy-2'-naphthyl) acetaldoxime.

Similarly, by employing the 2-(2'-naphthyl) acetaldehdye derivatives prepared in Examples 1, 2, 3 and 4 in the above process, the corresponding oxime derivatives thereof can be obtained. For example, 2-(5'-methyl-2'-naphthyl) acetaldoxime is prepared by using 2-(5'-methyl-2-naphthyl) acetaldehyde in the above process.

1-Methoxyimino-2-(6'-methoxy-2'-naphthyl) ethane, 1-ethoxyimino-2-(6'-methoxy-2'-naphthyl) ethane, 1-i-propoxyimino-2-(6'-methoxy-2'-naphthyl) ethane & 1-benzyloxyimino-2-(6'-methoxy-2'-naphthyl) ethane, are prepared by employing methoxyamine, ethoxyamine, i-propoxyamine and benzyloxyamine; respectively, in place of hydroxylamine in the above described process.

EXAMPLE 9

A mixture of 201 g. of 2-(7'-methyl-2'-naphthyl) acetaldehyde, 200 g. of acetic anhydride, 68 g. of borontrifluoride are stirred for 8 hours at about 5° C. The resulting reaction mixture is evaporated under reduced pressure to yield 2-(7'-methyl-2'-naphthyl) ethylidenediacetate.

In a similar manner, the acylals of the 2-(2'-naphthyl) acetaldehyde derivatives prepared in Examples 1, 2, 3 and 4 are prepared by means of the above described process. For example, 2-(5'-methylthio-2'-naphthyl) ethylidenediacetate is prepared from 2-(5'-methylthio-2'-naphthyl) acetaldehyde by means of the above process.

2-(5'-Methoxy-2'-naphthyl) ethylidenedipropionate, 2-(5'-methoxy-2'-naphthyl) ethylidenedicaproate, 2-(5'-methoxy-2'-naphthyl) ethylidenedivalerate, and 2-(5'-methoxy-2'-naphthyl) ethylidenesuccinate are prepared by utilizing propionic anhydride, caproic anhydride, valeric anhydride and succinic anhydride, respectively, in place of acetic anhydride in the above described process.

EXAMPLE 10

To a refluxing mixture of 18.5 g. of 2-(7'-methylthio-2'-naphthyl) propionaldehyde, 18.5 g. of hydrazine and 350 ml. of ethanol, there is added 5 drops of glacial acetic acid. The mixture is refluxed for an additional 5 minutes and sufficient ethanol is added to obtain a clear refluxing solution. The solution is cooled and filtered. The resulting crystals are thoroughly washed with cold (0° C) ethanol. The crystals are recrystallized from ethanol to yield the hydrazone or 2-(7'-methylthio-2'naphthyl) propionaldehyde.

Similarly, the hydrazones of the 2-(2'-naphthyl) acetaldehyde derivatives of Examples 1, 2, 3 and 4 are prepared by means of the above described process. For example, the hydrazone of 2-(4'-chloro-2'-naphthyl)-2,2-methyleneacetaldehyde is prepared is prepared from 2-(4'-chloro-2'-naphthyl)-2,2-methylene acetaldehyde by means of the above described process.

EXAMPLE 11

Part A A mixture of 21.5 g. of 2-(6'-methoxy-2'-naphthyl) propionaldehyde and 500 ml. of methylene chloride are cooled to 0° C and saturated with anhydrous ammonia. The mixture is stirred for 12 hours while maintaining the temperature at 0° C and continuing to bubble in ammonia. The resulting reaction mixture is then evaporated to yield 1-amino-2-(6'-methoxy-2'-naphthyl) propanol.

Part B The above product is warmed to 50° C under vacuum for 8 hours to yield 1-imino-2-(6'-methoxy-2'-naphthyl) propane.

In a similar manner, the amino alcohols and aldimines of the 2-(2'-naphthyl) acetaldehyde derivatives of Examples 1, 2, 3 and 4 are prepared by means of the above described process. For example, 1-imino-2-(1'-ethyl-2'-naphthyl)-2,2-difluoromethyleneethane is prepared from 1-amino-2-(1'-ethyl-2'-naphthyl)-2,2-difluoromethyleneethanol by means of the process described in Part B above, and 1-amino-2-(1'-ethyl-2'-naphthyl)-2,2-difluoromethyleneethanol is prepared from 2-(1'-ethyl-2'-naphthyl)-2,2-difluoromethylene acetaldehyde by means of the above process described in Part A described above.

1-Methylamino-2-(6'-methoxy-2'-naphthyl) propanol, 1-ethyl-amino-2-(6'-methoxy-2'-naphthyl) propanol, 1-i-propylamino-2-(6'-methoxy-2'-naphthyl) propanol, 1-benzylamino-2-(6'-methoxy-2'-naphthyl) propanol and 1-phenylamino-2-(6'-methoxy-2'-naphthyl) propanol are prepared by employing methylamine, ethylamine, isopropylamine, benzylamine, and phenylamine, respectively, in place of ammonia in the process described above in Part A. By employing the thus prepared alkyl-, aralkyl- and arylamino- 2-(6'-methoxy-2'-naphthyl) propanols in the process described above in Part B, 1-methylimino-2-(6'-methoxy-2'-naphthyl) propane, 1-ethylimino-2-(6'-methoxy-2'-naphthyl) propane, 1-i-propylimino-2-(6'-methoxy2'-naphthyl) propanem 1-benzylimino2-(6'-methoxy-2'-naphthyl) propane and 1-phenylimino-2-(6'-methoxy-2'-naphthyl) propane, respectively, are obtained.

EXAMPLE 12

To 600 ml. of a 40% solution of sodium bisulfite, is added 150 ml. of ethanol and 100 g. of 2-(6'-methoxy-2'-naphthyl) propionaldehyde in 500 ml. of ether. The resulting meixture is stirred for 3 hours; then it is filtered to yield the sodium bisulfite addition product of 2-(6'-methoxy-2'-naphthyl) propionaldehyde.

Similarly, the 2-(2'-naphthyl) acetaldehyde derivatives prepared in Examples 1, 2, 3 and 4 are employed in the above process to prepare the corresponding sodium bisulfite addition products thereof. For example, the sodium bisulfite addition product of 2-(5'-methoxy2'-naphthylI acetaldehyde is obtained by using 2-(5'-methoxy-2'-naphthyl) acetaldehyde in the above process.

EXAMPLE 13

To a mixture of 50 g. of borontribromide in 250 ml. of methylene chloride, cooled to -80° C, there is added 21.4 g. of 2-(6'-methoxy-2'-naphthyl) propionaldehyde. The mixture isallowed to warm to room temperature over one hour. The reaction mixture is then diluted with 250 ml. of water and filtered; the organic layer is then separated off. The organic layer is washed with water to neutrality, dried over sodium sulfate andevaporated to yield 2-(6'-hydroxy-2'-naphthyl) propionaldehyde.

By employing 2-(6'-methylthio-2'-naphthyl) acetaldehyde in the above process. 2-(6'-thio-2'-naphthyl) acetaldehyde is obtained.

Similarly, the methoxy, methoxymethyloxy, difluoromethoxy, methylthio, methoxymethylthio or difluoromethylthio substituted 2-(2'-naphthyl) acetaldehyde derivatives of Examples 1, 2, 3 and 4 are employed in the above process, give the corresponding hydroxy or thio substituted 2-(2'-naphthyl) acetaldehyde derivatives. For example, 2-(5'-thio-2'-naphthyl)-2,2-methyleneacetaldehyde is prepared from 2-(5'-isopropylthio-2'-naphthyl)-2,2-methuleneacetaldehyde by means of the above process.

EXAMPLE 14

The anti-inflammatory activity of 2-(6'-methoxy-2'-naphthyl) propionaldehyde was compared with that of phenylbutazone by means of a carageenin-induced rat paw inflammation test described by C. A. Winter et al., *The Proceedings of the Society for Experimental Biology & Medicine 111*, 544–47 (1962).

The test was modified in that female rats weight 80–90 grams were employed and the degree if inflammaton was measured one hour after the injection of carageenin in units of rear paw weight rather than rear paw volume. The results are shown in the following table.

| No. of Rats | Dose Range Tested mg./Rat | Relative Potency to Phenylbutazone (Phenylbutazone = 1) |
|---|---|---|
| 33 | 0.1 - 0.9 | 4 |

EXAMPLE 15

The analgesic activity of the bisulfite addition product of 2-(6'-methoxy-2'-naphthyl) propionaldehyde was compared with that of aspirin and phenylbutazone. The test used was based on the test of Randall & Selitto, *Arch. Int. Pharmacodyn* 111, 409–419 (1957) and consisted of administering orally by gavage 30 or 100 mg. per kilogram of body weight, the analgesic compound with water (20 ml. per kilogram of body weight) in eight male rats weighing between 120 to 200 grams. A control group received an equivalent volume of water. One hour after the administeration of the compound, 0.10 ml. of a 20% yeast suspension (Red Star Brand, primary dry type 600 in 0.9% saline) was injected into the sub-plantar area of the left hind paw of each rat in the drug treated group and the control group. The purpose of the injection is to provoke the formation of inflammatory edema.

Two hours after the injection of yeast, the control paw and the yeast inflammed paw of each rat in the drig treated group and in the control group successively were compressed at the plantar surface by a stud with a surface area of about 9 mm². attached to a force displacement transducer (model FTO3 Grass) which was driven at a constant rate. The induced pressure was recorded on a strip chart recorder. When a pain reaction was evoked from the rat by the application of pressure, the amount of pressure was recorded; the pressure was recorded in paper pressure.units (0 - 100). The difference between the amount of pressure required to evoke pain reaction between the control paw and inflammed paw among the drug treated group of rats and control group of rats serves as an index of analgesic activity. The measure of analgesic activity in the rats is expressed in percent, in reference to that of the inflammed paw and non-inflammed paw. [(Pressure units to evoke pain in inflammed paw/pressure units to evoke pain in control paw) × 100]. The results are summarized in the following table.

| Dose Administered in mg./kg. | Degree of Analgesic in percent with Reference to the Controls | | |
|---|---|---|---|
| | The bisulfite addition of 2-(6'-methoxy-2'-naphthyl) acetaldehyde | Aspirin | Phenylbutazone |
| 0 | 53 | 33 | 37 |
| 30 | 129 | — | 40 |
| 90 | — | — | 72 |
| 100 | 113 | 34 | — |

EXAMPLE 16

The analgesic activity of several 2-(2'-naphthyl) acetaldehyde derivatives was compared with that of aspirin and phenylbutazone. The test was based on the test of Randall & Sellitto, *Arch. Int. Pharmacodyn* 111, 409–419 (1957) and consisted of administering orally by gavage 30, 90 or 100 mg. per kilogram of body weight, the analgesic compound with water (20 ml. per kilogram of body weight) in eight male rats weighing between 120 to 200 grams. A control group received an equivalent volume of water. One hour after the administration of the compound, 0.10 ml. of a 20% yeast suspension (Red Star Brand, primary dry type 600 in 0.9% saline) was injected into the sub-plantar area of the left hind paw of each rat in the drug treated group and the control group. The purpose of the injection is to provoke the formation of inflammatory edema.

At hour one after the injection of yeast, the control paw and the yeast inflammed paw of each rat in the drug treated group in the control group successively were compressed at the plantar surface by a stud with a surface area of about 9 mm². attached to a force displacement transducer (model FTO3 Grass) which was driven at a constant rate. The induced pressure was recorded on a strip chart recorder. When a pain reaction was evoked from the rat by the application of pressure, the amount of pressure was recorded; the pressure was recorded in paper pressure units (0 – 100). The difference between the amount of pressure required to evoke pain reaction between the control paw and inflammed paw among the drug treated group of rats and control group of rats serves as an index of analgesic activity. The measure of analgesic activity in the rats is expressed in percent, in reference to that of the inflammed paw and non-inflammed paw. [(Pressure units to evoke pain in inflammed paw/pressure unit to evoke pain in control paw) × 100]. The results are summarized in the following table.

| Compound | Dose Administered in mg./kg. | Degree of Analgesia Percent with Reference to the Controls |
|---|---|---|
| 2-(6'-methoxy-2'-naphthyl)-propionaldehyde | 0 | 23 |
|  | 100 | 69 |
| hydroxyimino 2-(6'-methoxy-2'-naphthyl) propane | 0 | 75 |
|  | 100 | 96 |
| semicarbazone of 2-(6'-methoxy-2'-naphthyl) propionaldehyde | 0 | 14 |
|  | 100 | 78 |
| 1,1-dimethoxy-2-(6'-methoxy-2'-naphthyl) proprioaldehyde | 0 | 75 |
|  | 30 | 110 |
| bisulfite addition product of 2-(6'-methoxy-2'-naphthyl) propionaldehyde | 0 | 75 |
|  | 30 | 87 |
|  | 100 | 105 |
| aspirin | 0 | 44 |
|  | 100 | 62 |
| phenylbutazone | 0 | 41 |
|  | 30 | 66 |
|  | 90 | 78 |

EXAMPLE 17

The anti-pyretic activity of 2-(6'-methoxy-2'-naphthyl) propionaldehyde was compared to the anti-pyretic activity of aspirin.

Anti-pyretic activity - Female rats weighing 90–100 grams were used. The "normal" rectal temperature of the rats was recorded at hour 0, followed by the injection of 2 ml. of yeast suspension (the yeast suspension is prepared by suspending on cake of Fleischman's yeast in 22 ml. 0.9% NaCl) subcutaneously (1 ml. dorsally, 1 ml. ventrally). The injection sited are massaged to spread the suspension beneath the skin. The yeast injection induces elevated body temperature. At hour 17, the rats were massaged again to stimulate a further increase in body temperature. (It was found that handling the rats at the time the second temperature was taken resulted in a rise in body temperature.) At hour 18, the second rectal temperature was recorded, after which the test material was administered orally by gavage in 1 ml. aqueous vehicle. (The aqueous vehicle consists of 0.9% NaCl, 0.4% polysorbate 80, 0.5% carboxymethyl cellulose, 0.9% benzyl alcohol and water.) The thrid rectal temperature was obtained two hours after administration of the test material.

The degree of anti-pyretic activity was measured as a reduction in temperature (°F) from the second to the third temperature readings (temperature at hour 18 - temperature at hour 20) with respect to a control. The results are shown in the following table.

| Compound | No. of Rats | Doses Tested mg./rat | Relative Potency to Aspirin (Aspirin=1) |
|---|---|---|---|
| 2-(6'-methoxy-2'-naphthyl) propionaldehyde | 10 | 0.2 & 0.6 | 15 |

EXAMPLE 18

| Ingredients | Quantity per tablet, mgs. |
|---|---|
| 2-(7'-methyl-2'-naphthyl) propionaldehyde | 5 |
| sucrose | 245 |

The above ingredients are thoroughly mixed and processed into single scored tablets, one tablet being administered every three to four hours.

EXAMPLE 19

| Ingredients | Quantity per tablet, mgs. |
|---|---|
| 2-(6'-methoxy-2'-naphthyl) propionaldehyde | 60 |
| cornstarch | 38 |
| lactose | 150 |
| magnesium stearate | 2 |

The above ingredients are mixed intimately and pressed into single scored tablets.

EXAMPLE 20

| Ingredients | Quantity per capsule, mgs. |
|---|---|
| 2-(5'-methoxy-2'-naphthyl) propionaldehyde | 15 |
| lactose | 225 |
| dextrose | 10 |

The above ingredients are mixed and introduced into a No. 1 hard-shell gelatin capsule.

EXAMPLE 21

| Ingredients | Quantity per capsule, mgs. |
|---|---|
| 1,1-dimethoxy-2-(5'-methoxy-2'-naphthyl) ethane | 25 |
| lactose | 225 |

The above ingredients are mixed and introduced into No. 1 hard-shell gelatin capsule.

Similarly, the 2-(2'-naphthyl) acetaldehyde derivatives prepared in or by means of the processes of Examples 1-12 can be formulated as described above.

I claim:

1. 2-(5'-fluoro- 6'-methoxy-2'-naphthyl) propionaldehyde and the oxime thereof.
2. 2-(5'-chloro-6'-methoxy-2'-naphthyl) propionaldehyde and the oxime thereof.
3. 2-(5'-bromo-6'-methoxy-2'-naphthyl) propionaldehyde and the axime thereof.

* * * * *